(12) United States Patent
Beesley et al.

(10) Patent No.: US 7,718,443 B2
(45) Date of Patent: May 18, 2010

(54) ASSAY DEVICE

(75) Inventors: Natalie Elizabeth Beesley, Wellingborough (GB); Barry Sinclair Brewster, Royston (GB); Susan Catrin Day, Huntingdon (GB); Adrian Leslie Walker, St. Neots (GB)

(73) Assignee: Inverness Medical Switzerland GmbH, Zug (CH)

( * ) Notice: Subject to any disclaimer, the term of this patent is extended or adjusted under 35 U.S.C. 154(b) by 999 days.

(21) Appl. No.: 10/500,662

(22) PCT Filed: Jan. 9, 2003

(86) PCT No.: PCT/EP03/00274

§ 371 (c)(1),
(2), (4) Date: Feb. 10, 2005

(87) PCT Pub. No.: WO03/058243

PCT Pub. Date: Jul. 17, 2003

(65) Prior Publication Data
US 2005/0130322 A1    Jun. 16, 2005

(30) Foreign Application Priority Data

Jan. 9, 2002 (EP) .................. 02250119

(51) Int. Cl.
*G01N 33/53* (2006.01)
(52) U.S. Cl. .............. 436/514; 436/518; 436/169; 436/805; 436/810; 435/7.1; 435/7.9; 435/287.1; 435/805; 435/970; 422/56
(58) Field of Classification Search ................ 436/514, 436/518, 169, 805, 810, 7.1, 7.9; 435/287.1, 435/805, 970; 422/56
See application file for complete search history.

(56) References Cited

U.S. PATENT DOCUMENTS

| | | |
|---|---|---|
| 5,119,830 A | 6/1992 | Davis .................... 128/771 |
| 5,602,040 A | 2/1997 | May et al. .............. 436/514 |
| 5,620,863 A | 4/1997 | Tomasco et al. ........... 435/14 |
| 5,622,871 A | 4/1997 | May et al. .............. 436/514 |
| 5,656,503 A | 8/1997 | May et al. .............. 436/514 |
| 5,719,034 A | 2/1998 | Kiser et al. ............. 435/14 |
| 5,843,691 A | 12/1998 | Douglas et al. ........... 435/14 |
| 5,916,815 A | 6/1999 | Lappe ................... 436/92 |
| 5,976,895 A | 11/1999 | Cipkowski .............. 436/518 |
| 6,187,598 B1 | 2/2001 | May et al. .............. 436/514 |
| 6,228,660 B1 | 5/2001 | May et al. .............. 436/514 |
| 2001/0008774 A1 | 7/2001 | May et al. .............. 436/514 |
| 2001/0041368 A1 | 11/2001 | May et al. .............. 436/514 |
| 2002/0001852 A1 | 1/2002 | Mendel-Hartvig et al. .. 436/514 |

FOREIGN PATENT DOCUMENTS

| | | |
|---|---|---|
| EP | 0 560 411 A2 | 9/1993 |
| WO | WO 01/35094 A1 | 5/2001 |
| WO | WO 01/86302 A1 | 11/2001 |

OTHER PUBLICATIONS

Search Report for PCT/EP03/00274, Date of Search Jun. 4, 2003.

*Primary Examiner*—Bao-Thuy L Nguyen
(74) *Attorney, Agent, or Firm*—Foley Hoag LLP

(57) ABSTRACT

Disclosed is an assay device to determine the presence of at least one analyte of interest in a liquid sample, the device comprising means for generating a first signal (the 'test' signal) which indicates the presence and/or amount of analyte of interest in the sample; and means for generating a second signal, the generation of which second signal indicates both (a) the test has been successfully conducted, and that (b) sufficient time has elapsed following contact of the assay device with the liquid sample for the test to be read and the first signal to have been properly generated.

22 Claims, 1 Drawing Sheet

Figure 1 - Comparison of control line signal at 40 and 60 sec for nitrocellulose of different flow rates using 0 mIU/mL hCG urine standard
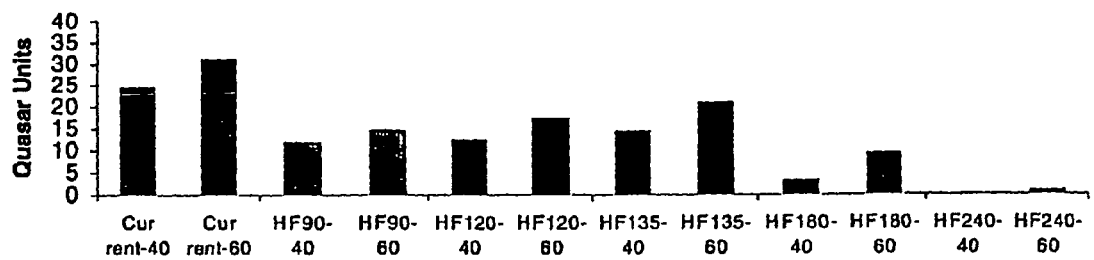
Figure 2 - Comparison of control line signal at 40 and 60 sec for nitrocellulose of different flow rates using 400 mIU/mL hCG urine standard
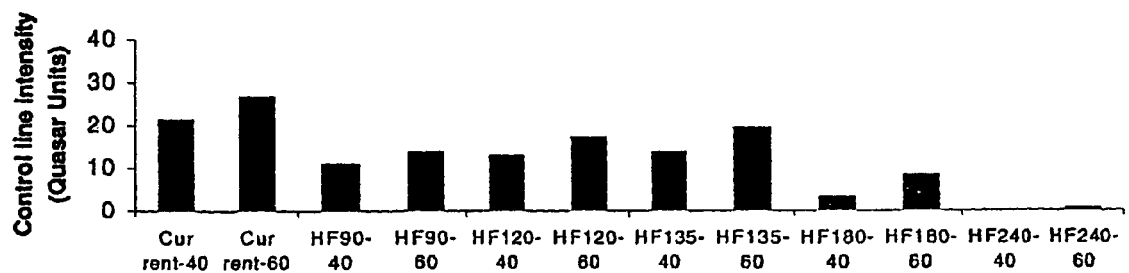
Figure 3
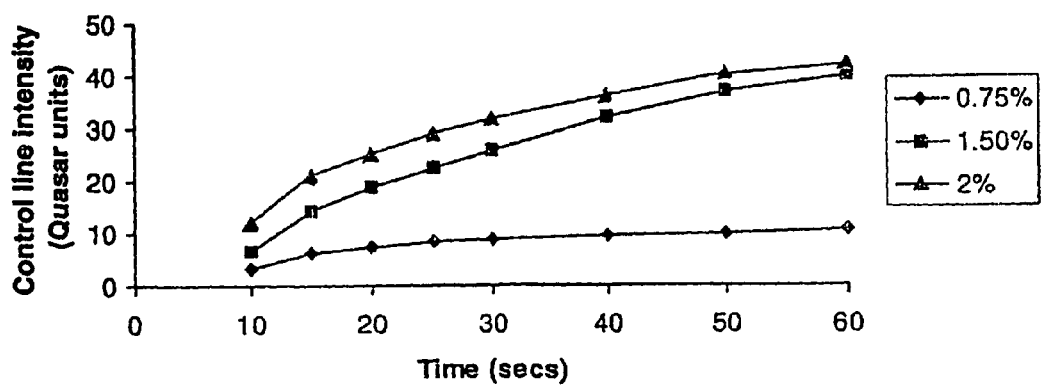

ASSAY DEVICE

FIELD OF THE INVENTION

The invention relates to an assay device, a method of performing an assay, and a method of making an assay device.

BACKGROUND OF THE INVENTION

Assay devices which employ immunochromatographic principles are well known. Particularly common are "lateral flow" assay devices. In devices of the lateral flow type, a labelled specific binding reagent is releasably immobilised on a strip of porous material. A liquid sample is applied to one end of the porous strip and the capillary properties of the strip transports the liquid sample along the strip, releasing the labelled specific binding reagent, which binds specifically to the analyte of interest (at a first binding site thereof), if present, in the sample. The labelled binding reagent is then generally captured at a test zone by a second reagent having specific binding for a second binding site of the analyte of interest. Excess labelled binding reagent is then typically captured at a control zone, downstream of the test zone by a control reagent which binds specifically to the labelled reagent. Assay devices of this type are described in further detail in, for example EP 0 291 194.

In a known lateral flow assay device (of the sort disclosed in EP 0 291 194 and EP 0 560 411), such as the Clearblue® pregnancy test kit (available from Unipath Ltd, Bedford UK), which works by detecting the presence of hCG in a urine sample applied to the test device, two visible signals may be generated. One signal is a 'control' signal, and is formed by the localization of derivatised blue latex beads: the latex beads are coated with an immunoglobulin molecule and are captured by a capture antibody, deposited in a line on the test stick generally perpendicular to the direction of sample flow, the capture antibody having specific binding activity for the immunoglobulin carried on the beads. The generation of this signal informs the user that:

(i) neither the immunoglobulin on the latex bead, nor the capture antibody on the test stick, have been sufficiently denatured or otherwise degraded during manufacture or storage of the test kit significantly to interfere with the specific binding between the two molecules; and (ii) sufficient liquid sample has been applied to mobilise the releasably immobilised latex beads and to transport them along the test stick at least as far as the "control" zone, in which the capture antibody is located.

The significance of (i) is that the immunoglobulin on the test stick is one which binds specifically to the analyte of interest. The control signal indicates that the capture antibody and the latex-bound antibody are still capable of associating, which implies that other immunoglobulin-based reagents (such as an analyte-specific immunoglobulin reagent) in the test kit should equally have retained their specific binding activity. The significance of (ii) is that the 'control' zone is located downstream of the 'test zone', in which the analyte is bound (together with any specifically-associated latex-labelled immunoglobulin) by a further analyte-specific immunoglobulin, deposited in a line on the test stick, generally perpendicular to the direction of flow of the sample. The line of immobilised analyte-specific immunoglobulin in the test zone is substantially parallel to, but upstream of, the line of immobilised antibody in the control zone.

In this way, a urine sample containing hCG contacted with the test stick in a correctly-performed assay, will cause the deposition of latex beads in both the control zone and in the test zone, resulting in the formation of two blue lines visible to the user, one line in the control zone and one line in the test zone.

The instructions provided with the kit direct the user to read the assay result 1 minute after removing the test stick from contact with the sample. Accordingly it is necessary for the user to have access to an external timer in order to read the assay result after the correct time interval has elapsed.

The label is generally a direct label, which is readily visible to the naked eye, so that a visual signal is generated wherever the labelled reagent accumulates in sufficient amount.

A problem with this type of assay device is that it takes a little while, after removing the assay device from contact with the liquid sample, for the test signal to appear. Clearly the user would like to read the result of the assay as soon as possible but, equally, the user requires confidence that sufficient time has elapsed for the proper assay result to have been obtained and that the test is not being read too early, without having to wait an inordinately long period.

In order to address this problem, it is known to incorporate a "timer" into an assay device, as described in EP 0 826 777. In particular, EP 0 826 777 discloses an assay device which comprises, in addition to the usual assay reagents, a variety of components which interact a pre-determined time interval after application of the sample to the test device, to create a detectable colour change. These additional 'timer' reagents are deposited in a 'timer' section of the test strip and, upon hydration by the sample, interact to produce a colour change.

In addition, the 'timer' reagents are also said to perform quality-control function. It is generally undesirable if assay devices are exposed to moisture. However, since the timer reagent when hydrated produces a coloured product, the timer will reveal if the device has been exposed to moisture. The 'quality control' function is however very limited, as it indicates only that the device has been exposed to an unquantified amount of moisture. The arrangement disclosed in EP 0 826 777 cannot indicate, for example, whether the test reagents have retained their specific binding properties, which can deteriorate with time, especially if the assay device has been stored in conditions of temperature, for instance, which are sub-optimal.

SUMMARY OF THE INVENTION

In a first aspect the invention provides an assay device to determine the presence of at least one analyte of interest in a liquid sample, the device comprising means for generating a first signal (the 'test' signal) which indicates the presence and/or amount of analyte of interest in the sample; and means for generating a second signal, the generation of which second signal indicates both that (a) the test has been successfully conducted, and (b) sufficient time has elapsed following contact of the assay device with the liquid sample for the test to be read and the first signal to have been properly generated.

Preferably the assay device is of the immunochromatographic type, more especially a lateral flow immunochromatographic assay device.

The analyte of interest may be any suitable molecule such as a polypeptide or peptide, nucleic acid, steroid or the like, Conveniently the analyte is a hormone. In a particular embodiment the analyte is a sex hormone such as luteinising hormone (LH) or a pregnancy-associated hormone, such as human chorionic gonadotrophin (hCG) In other embodiments the analyte of interest may be a drug of abuse, such as an opiate, amphetamine or cocaine.

The liquid sample may be an environmental liquid (e.g. water from a source such as a river, lake or ocean, or an aqueous solution) but more preferably is a sample of a body fluid comprising, for example, blood, plasma, serum, saliva, urine, sweat, lachrymal fluid, vaginal fluid and the like. Of the foregoing, urine is the preferred sample, since it can be readily obtained without invasive sampling techniques and is a relevant sample for the preferred analyte, hCG.

The first and/or second signals may, for instance, be visible signals. Generally it is preferred that both the first and second signals are visible signals. The means for generating the respective first and second signals will generally be of conventional type. For instance, the first or 'test' signal and the second signal may both be formed by the capture or localisation of coloured latex beads or other directly-labelled specific binding reagent, generally as disclosed in EP 0 291 194 and EP 0 560 411. It will be apparent to those skilled in the art that the test device may be used to test for the presence of more than one analyte of interest in a sample. For example, two different analyte-specific binding reagents may be provided on the device, each specific for a respective analyte of interest. The "first" test signal may therefore comprise, in some embodiments, a plurality of different signals, each signal corresponding to the presence or absence of a respective analyte. The term "first signal" should therefore not be construed as being limited to the generation of a single test signal.

In addition, it is at least possible that the "second" signal may itself comprise a plurality of signals. For example, whilst it is preferred for the second signal to be generated at a single location, it is also possible for the second signal to be generated at two different locations on the assay device e.g. a "control" zone which indicates the control signal, and a "timer" zone which indicates the "timer" signal. In such embodiments, where the two components of the second signal are generated at different locations, it is preferred that the control signal and the timer signal are generated (a) substantially simultaneously (i.e. within 1-5 seconds of each other) and/or (b) by the same signal-generating reagent. One means, for example, for obtaining substantially simultaneous generation of a two-component control/timer signal is to provide the control zone and the timer zone at points on the assay device which are reached substantially simultaneously by the respective control and timer signal-generating reagents. Where the control and timer signal-generating reagents have substantially the same rate of progression along the test stick, the control and timer zones may be provided in a side-by-side relationship.

Prior art assay devices, such as the assay device provided in the Clearblue® test kit include means for generating a first, 'test', signal and a second 'control' signal, the second signal indicating that the test has been successfully conducted. However, in the assay device provided in the Clearblue® test kit there is no means of ensuring that the control signal appears only after a specific, pre-determined interval following contact of the assay device with the sample, and which coincides with the desired time point at which the assay result is intended to be read. In contrast, it is an essential requirement of the present invention that the signal which acts as a control signal (i.e. that indicates that the test reagents retain sufficient functionality and specific binding property for a meaningful test result to be obtained) to indicate that the test has been successfully conducted will only be generated a specific, pre-determined time after the device has been contacted with the sample, which time also coincides with the time point at which the assay result is intended to be read.

In this way, the second signal not only acts as a control signal but also as an integral assay "timer". In use therefore the assay device gives rise to a signal which has at least two distinct purposes.

In particular, it is necessary for the assay device of the invention to be arranged so that the second signal (the dual-purpose control/timer signal) is formed only at a time when the first signal (the test signal) will have been properly formed i.e. a positive test signal if the analyte of interest is present in the sample, and a negative test signal (which can be relied on with confidence) if the analyte is not present or is present at a concentration beneath the minimum sensitivity claimed for the assay device. In practice a negative result is normally indicated by the non-appearance of a visible signal in the test zone.

A typical assay device, such as the Clearblue® pregnancy test kit, is ready to be read about 1 minute after removing the device from contact with the sample, the device usually being held in a urine stream for about 5 seconds. In preferred embodiments therefore an assay device in accordance with the present invention will give rise to the second signal about 1 minute after the device is removed from contact with sample. However, other assay devices may normally be read after other time intervals (e.g. anything from 30 seconds to 5 minutes) and in other embodiments therefore the second signal may be formed at a time more or less than 1 minute after contact with the sample.

A great variety of methods may be employed to control the time which elapses between contacting the assay device with the sample and the formation of the second signal. These include, but are not limited to:

methods which modulate the time taken for sample to be transported to the control zone and/or methods which modulate the time taken for the latex bead or other signal-generating reagent to reach the control zone.

In the Clearblue® assay device, the second signal (i.e. the 'control' signal) generally appears about 20 seconds after removing the assay device from contact with the sample. Accordingly, in order to modify a conventional Clearblue® assay device to conform to the requirements of the present invention it would be necessary to delay the appearance of the second signal by about 40 seconds, in order to indicate to the user when 1 minute had elapsed and that the test result was ready for reading.

Methods of achieving such a delay in the appearance of the second signal include one or more ways of reducing the flow rate of the sample and/or signal-generating reagent(s) within the device, such as:

(i) increasing the size of the latex bead or other moiety attached to the signal-generating reagent;
(ii) altering the theological properties of the sample e.g. by incorporating a flow rate inhibitor into the assay device—this could comprise, for example, incorporating an effective amount of a polyhydric compound, such as a sugar (e.g. sucrose) or other viscosifier into the wick or other portion of the device, the compound being resuspended upon contact with the sample and altering the theological properties thereof, specifically the viscosity of the sample;
(iii) altering the flow properties of the assay device e.g. by selecting a membrane with different flow properties (e.g. different porosity and/or of different material) or by laminating one or both surfaces of the membrane (typically lamination only of the upper surface: that is, the surface which is further from the observer when the assay result is read). It may be desirable to use an assay device which comprises a test strip composed of two parts: an upstream part with a membrane of relatively high flow rate, and a downstream part between the test zone and the control zone, with a membrane of relatively low flow rate.

Alternatively, a delay in the appearance of the second signal could be obtained by increasing the distance the sample (together with resuspended signal-generating reagent) is required to migrate within the assay device before arriving at the control zone. This can be effected simply by moving the control zone further downstream, away from the wick. Another approach is to have the second signal appear at substantially the same time as in the conventional Clearblue® device but to decrease the time taken for the test reaction to produce the first signal in the test zone. This may be effected by moving the test zone further upstream, towards the wick. In either approach, the net result is to increase the spatial (and hence temporal) separation between the test and control zones, so that the test and control signals are simultaneously ready for reading.

Another type of approach does not affect the generation of the signal, but rather aims to impose a delay upon its detection or perception by a user. Thus, for example, where the second signal is the appearance of a coloured line, spot or other mark or visible signal, the desired effect can be obtained by increasing the delay before the generated visible signal is seen by a user. For instance a translucent covering may be applied to the control zone thus incompletely obscuring the control zone to the user. This may be accomplished, for example, by applying a translucent layer of plastics laminate or other material to the lower surface of the control zone (i.e. that side of the test stick which is examined by a user to read the assay result). Suitable materials include ARcare® 7823 (available from Adhesives Research Europe Ltd, Great Dunmow, Essex, UK), and S/S "frosted silver" laminate, (available from Davies Industrial Supplies, Letchworth, Herts, UK).

It will be apparent to those skilled in the art that none of the methods discussed above are mutually exclusive and any of the methods may be used in isolation or in conjunction with any one or more further methods. Moreover the list is in no way intended to be exhaustive, and other methods of achieving the desired objective may be apparent to those skilled in the art given the benefit of the present disclosure.

It will also be apparent that, in those embodiments where it may be desired to decrease the time taken for the second signal to be generated, then generally doing the opposite of the methods outlined above will achieve the desired effect.

A further significant preferred feature of the invention is to reduce what may be termed as the "signal development" time. This is the period of time taken for the second signal to develop, from its initial appearance, perceivable by some observers (say, less than 20%), into an unambiguous clear signal perceivable by over 95% of observers (selected at random from the human population). Thus, for example, the control signal of the conventional Clearblue™ assay device has a relatively long signal development time, taking about 15 seconds to develop from the first faint blue tinge in the control zone to a strong, definite blue mark which is readily apparent. Whilst this is acceptable where the signal performs merely the single function of acting as a control indicator, a long signal development time is undesirable where the signal is also intended to act as a timer, since it introduces uncertainty into the mind of the user as to when the assay test result should be read (e.g. upon initial perception of the second signal, or upon its perceived completion of development, or at some intermediate point during the intervening 15 seconds development time?).

Accordingly, it is a preferred feature of the present invention that the signal development time of the second signal is less than 15 seconds, preferably less than 12 seconds, more preferably less than 10 seconds, and most preferably less than 8 seconds. In general, the shorter the signal development time the better, so as to give an almost instantaneous indication to the user when to read the assay result.

Several methods of decreasing the signal development time have been devised by the inventors. One technique is to apply a separate depot of control latex-labelled antibody (or other labelled control signal-generating reagent in other embodiments) closer to the control zone and/or in a more closely defined area This is found effective because the control latex, when resuspended by uptake of sample, tends to become rather dispersed during its migration along the assay device, so that the control latex arrives at the control zone over an extended period. This dispersion can be reduced by decreasing the distance the control latex must travel before arriving at the control zone. Thus, for example, in one embodiment the time taken for the second signal to be formed can be increased by shifting the control zone downstream, whilst, at the same time, the signal development time can be decreased by depositing the control latex closer to the control zone.

Another, more preferred, method of reducing the signal generation time is to increase the amount of control latex applied to the assay device. This is conveniently achieved by increasing the concentration of the suspension of control latex applied to the assay device.

About 2% w/v latex is particularly suitable which, for a typical embodiment, would result in the deposition of about 22 µg of control latex per assay device.

In a second aspect the invention provides a method of performing an assay, comprising use of an assay device in accordance with the first aspect of the invention defined above.

The various features of the invention will now be described further by way of illustrative example and with reference to the accompanying drawings, in which:

FIGS. 1 and 2 are bar charts comparing the intensity of control signal generated after 40 or 60 seconds using assay devices comprising various nitrocellulose membranes; and FIG. 3 is a graph of control signal intensity (arbitary "Quasar" units) against time (seconds).

EXAMPLES

Example 1

Modulating Time for Formation of Second Signal (Adjusting the "Timer")

A number of experiments were performed to demonstrate the feasibility of altering the delay between contacting an assay device with the sample and the formation of the second signal in the control-zone. As a model, the inventors used the Clearblue® pregnancy test kit, commercially available from Unipath Ltd (Bedford, UK).

In the context of the Clearblue® device, it would be necessary for the control signal to form 60 seconds after contacting the assay device with a urine sample, in order for the signal to indicate additionally to a user that the desired amount of time had elapsed and that the assay result was ready to read. Preliminary tests showed that, with the existing Clearblue® device, the control signal generally appeared 20-25 seconds after an initial (20 second) incubation with a urine sample. Accordingly, in order to modify the existing device it would be necessary to delay the appearance of the second signal by 35-40 seconds.

Various approaches were investigated with a view to obtaining the desired delay in appearance of the second signal.

1.1 The First Approach was Movement of the Control Zone Downstream, Further away from the Wick.

Tests were carried out to determine the position on the device that the sample front reached at 1 minute. The value obtained was 25.0 mm measured from the bottom of the nitrocellulose.

With the control line at 16.5 mm measured from the bottom, downstream end, of the nitrocellulose strip (the position of the control line in the current Clearblue® device) using 0.75% w/v solids latex and a 20 second incubation time for contacting with a urine sample. then after 10 seconds the control line signal was already visible with an intensity of 5 Quasar (arbitary) units and after 60 seconds the intensity was at 12-13 Quasar units. (By way of explanation the Quasar™ apparatus is a device used by the inventors for quantifying the intensity of visible signals generated by lateral flow test sticks: a light is shone through the test stick and the intensity of light is measured by a detector on the other side of the test stick: the proportion of light absorbed [and hence the intensity of the test signals] is assessed by comparing the amount of light transmitted through the device in the presence and absence of the signal on the stick). With the control line at 25.0 mm, the intensity at 10 seconds was approximately 1 Quasar unit and was between 6 and 8 Quasar units at 60 seconds, and it took 40 seconds to attain an intensity of 3-5 units i.e. the lowest intensity at which naive readers perceived a control line. Therefore moving the control line position from 16.5 mm to 25.0 mm significantly delayed control line formation.

1.2 Slower Running Nitrocellulose

It was proposed that using a slower flowing nitrocellulose membrane than that currently used for the Clearblue® device might retard control signal formation. The flow rate of nitrocellulose is controlled by the pore size, and this in turn is controlled either by the amount of water in the nitrocellulose mix (to control flow rates within a small range) or by changing the whole mix of the nitrocellulose (i.e. incorporating varying amounts of detergents, surfactants, water and nitrocellulose), to cause a major alteration of flow rate. A number of membranes from both Schleicher and Schuell GmbH ("S&S" Dassel, Germany) and Millipore were tested: S&S 170/100, and the Millipore HiFlow membrane range: HF75, HF90, HF120, HF135, HF180, HF240.

The S&S 170/100 membrane was used in an experiment with 100 nm diameter latex particles. It was found that the 100 nm latex was able to flow up to the control line position (16.5 mm) of the 170/100 nitrocellulose membrane within 1 minute, but that 380 nm latex particles (the size used in the conventional Clearblue® device) took more than 5 minutes to reach the control zone. Accordingly, use of the S&S 170/100 membrane might be suitable in conjunction with smaller sized latex particles.

An experiment was also conducted on control line generation using each speed of nitrocellulose from the HiFlow range (HF75, HF90, HF120, HF135, HF180, and HF240) of nitrocellulose membranes available from Millipore corporation (Bedford, Mass., USA). The numbers relate to the time taken in seconds for liquid to flow 4 cm up the strip when tested in the Millipore laboratories.

The characteristics desired for the nitrocellulose membrane were that the control line could not be seen at 40 seconds (i.e. <5 Quasar units) after incubation with the sample but could be seen at 60 seconds (i.e. >5 Quasar units).

An intensity of 5 Quasar units was taken as being the minimum signal intensity discernible by a naive reader. The various membranes were tested with a urine sample without hCG and with a urine sample which contained hCG at a concentration of 400 mIU/ml. The results are shown in FIGS. 1 and 2 respectively.

FIGS. 1 and 2 are bar charts showing the intensity of the control zone signal (measured in arbitary "Quasar" units) after 40 or 60 seconds, following incubation with a urine sample devoid of hCG (FIG. 1) or containing hCG at 400 mIU/ml (FIG. 2), for the current Clearblue® device and for each of equivalent devices prepared using a different Millipore nitrocellulose membrane with a different flow rate.

The Figures show that the membrane best matching the desirable criteria was HF180, which gave a control zone signal with an intensity below 5 units after 40 seconds, but a signal of about 10 units after 60 seconds, regardless of whether the sample under test contained hCG.

1.3 Partial Obscuration of the Control Zone

If the control line were allowed to form as normal but its perception by the consumer could be sufficiently retarded, then it would be possible to delay the effective appearance of the control signal. The perception of the control line by the user could be retarded by laminating a translucent material over the area of the control zone. This would mean that only a sufficiently intense control line could be seen in the control zone by the user.

A backing laminate (ARcare® 7823, from Adhesives Research Europe Ltd) was secured in position (using adhesive tape) so as not to cover the test zone, (therefore the appearance of the test line itself was not altered), but covering the control zone. The laminate used was translucent, with a milky appearance and was placed on the side seen through the control window. This laminate slowed down the perception of the control line generation by blocking out approximately 5 Quasar units worth of signal intensity and therefore delaying visibility of the control line for the existing Clearblue® from 20 seconds to 30 seconds. Samples of other laminate materials are currently under investigation.

Example 2

Decreasing Signal Development Time

As explained above, when the control signal is also performing a timer function, as in the current invention, it is desirable that the signal development time is minimised. The inventors performed some experiments to investigate reducing the signal development time, in the context of the conventional Clearblue® assay device.

The conventional Clearblue® product contains approximately 7.6 µg of control latex, applied to the device from a 0.5% w/v latex suspension. Test latex will also bind to control line. The inventors wished to determine if increasing the amount of control latex deposited on the device would decrease the control signal development time. An experiment was performed in which control latex was deposited onto an assay device from a suspension of 0.75, 1.50 and 2.0% (w/v) latex, and the signal development time compared. The results are shown in FIG. 3, which is a graph of signal intensity ("Quasar" units) against time.

FIG. 3 shows that it took 15 seconds for the control line to develop an intensity which could be seen by naive readers (i.e. 5 units) with control latex from a 0.75% suspension. It took less than 10 seconds for the control line to develop to the same intensity when latex at 2.0% w/w solids was deposited. The results also showed that the intensity of the control line at 60 seconds was greatly increased from the intensity of 11 Quasar units obtained using latex at 0.75% solids to 42 Quasar units obtained using latex at 2.0% solids.

The invention claimed is:

1. An assay device to determine the presence of at least one analyte of interest in a liquid sample, the device comprising a test strip on which is deposited:
   a first latex-labeled analyte-specific binding reagent for generating a first signal, or 'test' signal, which indicates the presence and/or amount of analyte of interest in the sample; and
   a second latex-labeled specific binding reagent from a control latex suspension having a latex concentration of at least 1.5% w/v for generating a second signal, the generation of which second signal indicates both
   (a) the test has been successfully conducted, and that
   (b) sufficient time has elapsed following contact of the assay device with the liquid sample for the test to be read and the first signal to have been properly generated.

2. The device of claim 1, wherein the analyte of interest is hCG.

3. The device of claim 1, wherein the device is a lateral flow immunochromatographic assay device.

4. The device of claim 1, wherein the second signal has a signal development time of about 1 minute.

5. The device of claim 1, wherein the second signal is a visible signal which appears in a portion of the test device covered by a layer of translucent material.

6. The device of claim 1, wherein the second signal has a signal development time of less than 10 seconds.

7. The device of claim 6, wherein the second signal has a signal development time of less than 8 seconds.

8. A method of performing an assay to determine the presence of an analyte of interest in a sample, the method comprising the steps of: contacting an assay device according to claim 1 with the sample; observing the appearance of the second signal; observing the appearance of the first signal when the second signal has appeared; and concluding that the analyte of interest is present in the sample if the first signal appears when the second signal has appeared.

9. The method of claim 8, wherein the sample is a sample of body fluid.

10. The method of claim 9, wherein the sample is urine.

11. The method of claim 8, wherein the analyte of interest is hCG.

12. The device of claim 1, wherein the sufficient time is a pre-determined time.

13. The device of claim 1, wherein the second latex-labeled specific binding reagent is deposited on the test strip at a position more than 16.5 mm measured from a position at which the liquid sample is to be applied to the test strip.

14. The device of claim 13, wherein the second latex-labeled specific binding reagent is deposited on the test strip at a position less than or equal to 25 mm measured from a position at which the liquid sample is to be applied to the test strip.

15. The device of claim 1, wherein the second latex-labeled specific binding reagent is deposited on the test strip at a position less than or equal to 25 mm measured from a position at which the liquid sample is to be contacted to the test strip.

16. The device of claim 1, further comprising a laminate placed over the deposit of second latex-labeled specific binding reagent.

17. The device of claim 16, wherein the laminate comprises a translucent laminate.

18. The device of claim 1, wherein the device comprises up to about 22 micrograms of second latex-labeled specific binding reagent.

19. The device of claim 1, wherein the first latex-labeled analyte-specific binding reagent comprises a first antibody specific for the at least one analyte of interest.

20. The device of claim 19, wherein the second latex-labeled specific binding reagent comprises a second antibody specific for a third antibody that is specific for the at least one analyte of interest.

21. The device of claim 1, wherein the test strip has a capillary flow time of about 180 seconds per 4 centimeters.

22. A method of making the device of claim 1, comprising:
   depositing the first latex-labeled analyte-specific binding reagent on the test strip; and
   depositing the second latex-labeled specific binding reagent on the test strip from a control latex suspension having a latex concentration in the range of about 1.5% to 2% w/v.

* * * * *